United States Patent [19]

Higginbotham et al.

[11] Patent Number: 4,495,809

[45] Date of Patent: Jan. 29, 1985

[54] DEEP DEPTH UNDEX SIMULATOR

[75] Inventors: Robert R. Higginbotham, Portsmouth; Alexander Malakhoff, Arlington, both of Va.

[73] Assignee: The United States of America as represented by the Secretary of the Navy, Washington, D.C.

[21] Appl. No.: 480,180

[22] Filed: Mar. 29, 1983

[51] Int. Cl.³ .................. G01N 33/22; G01N 37/00; G01M 10/00

[52] U.S. Cl. .................. 73/432 SD; 73/35; 73/148

[58] Field of Search .............. 73/12, 35, 148, 432 SD, 73/432 J, 432 V, 432 R

[56] References Cited

U.S. PATENT DOCUMENTS

| | | | |
|---|---|---|---|
| 2,754,677 | 7/1956 | New | 73/37 |
| 2,957,337 | 10/1960 | Choate et al. | 73/12 |
| 3,085,422 | 4/1963 | Monroe et al. | 63/12 |
| 3,373,716 | 3/1968 | Williams | 116/114 |
| 3,495,455 | 2/1970 | Allgood | 73/12 X |
| 3,613,435 | 10/1971 | Anderson | 73/37 |
| 3,729,980 | 5/1973 | Johnson et al. | 73/12 |

FOREIGN PATENT DOCUMENTS 847153  7/1981  U.S.S.R. .................. 73/12

OTHER PUBLICATIONS

The Naval Ship Research & Development Center, Report 3039, Nov. 1971, Captain M. da C. Vincent, USN, pp. 21–23, 25–27, 43, 44, 53 & 54.
Navord Report 6844 "Design Characteristics of a Conical Shock Tube for the Simulation of Very Large Charge Blasts (U)", William S. Filler; 16 pages; Oct. 1960.

Primary Examiner—Gerald Goldberg
Assistant Examiner—Tom Noland
Attorney, Agent, or Firm—R. F. Beers; L. A. Marsh

[57] ABSTRACT

A deep depth underwater simulator is illustrated for determining the dual effects of nuclear type underwater explosion shockwaves and hydrostatic pressures on a test vessel while simulating, hydrostatically, that the test vessel is located at deep depths. The test vessel is positioned within a specially designed pressure vessel followed by pressurizing a fluid contained between the test and pressure vessels. The pressure vessel, with the test vessel suspended therein, is then placed in a body of water at a relatively shallow depth, and an explosive charge is detonated at a predetermined distance from the pressure vessel. The resulting shockwave is transmitted through the pressure vessel wall so that the shockwave impinging on the test vessel is representative of nuclear type explosive shockwaves transmitted to an underwater structure at great depths.

1 Claim, 4 Drawing Figures

DEEP DEPTH UNDEX SIMULATOR

CROSS REFERENCE TO RELATED APPLICATION

This application is related to U.S. application Ser. No. 06/422,409 filed Sept. 23, 1983; and, having a Notice of Allowance dated May 9, 1984, and the Issue Fee was paid July 12, 1984, and now U.S. Pat. No. 4,479,378 to be issued on Oct. 30, 1984. This application claims the specific deep depth underwater shockwave and hydrostatic pressure simulator means for determining the dual effects of nuclear type underwater shockwaves and hydrostatic pressures on a test vessel located in shallow water. The related application now allowed, claims a method and apparatus for exprimentally determining response characteristics and strength capacity of submerged hull structures in shallow water.

BACKGROUND OF THE INVENTION

1. Field of the Invention

This invention relates to a deep depth underwater simulator means for determining the dual effects of nuclear type underwater explosion shockwaves and hydrostatic pressures on a test vessel while simulating hydrostatically, that the test vessel is located at deep depths.

The conventional method and system for determining the dual effects of underwater explosion shockwaves and hydrostatic pressures on a test vessel is to actually submerge the instrumented model and explosive charge from a support vessel to the desired depth and detonating the charge at a prescribed distance from the model. This method requires solving large logistical problems of personnel and equipment to properly authorized remote sites. Further, raising and lowering the test vessel and the explosive charge is time-consuming and thus very costly. Moreover, carefully laid out test plans are often disrupted by wave and weather conditions.

2. Description of the Prior Art

The prior art illustrates various testing means and systems for pressure structure. One inventor, New, in U.S. Pat. No. 2,754,677 illustrates nondestructive testing of thin shells by differential pressure. Specifically testing for determining incipient buckling pressures of thin shells subjected to external pressure. Choate, et al., in U.S. Pat. No. 2,957,337 illustrate hydrodynamic testing apparatus for use in testing hollow articles by means of pressure applied externally and internally. A hydrodynamic loader is illustrated in U.S. Pat. No. 3,085,422 for simulating sudden dynamic pressure loads. Williams, in U.S. Pat. No. 3,373,716 illustrates a shock indicating device. Specifically, the invention illustrates a shock indicating means for use with easily damageable apparatus wherein an inertial body ordinarily spherical, supported in a cavity of a block of material, on fingers extending from all sides of the cavity. A caused shock is administered causing the inertial body to crush and permanently compress certain of the fingers which is then inspected and measured to determine the degree and direction of the shock. Multiple units can be used. Anderson, in U.S. Pat. No. 3,613,435 illustrates a method and system for static testing structures utilizing an earth formation having a test chamber therein for static testing. And, Johnson, et al., in U.S. Pat. No. 3,729,980 illustrate a hydrodynamic shock simulator for providing an underwater shock environment for a sonar transducer under test.

SUMMARY OF THE INVENTION

The present invention provides a deep depth underwater shockwave and hydrostatic pressure simulator means for determining the dual effects of nuclear type underwater shockwaves and hydrostatic pressures on a test vessel located in a shallow water means comprising a test vessel filled with air at atmospheric pressure and positioned and suspended within a specifically designed pressure vessel, said pressure vessel containing fluid between the outer shell of the test vessel and the inner shell of the test vessel, a pressure means for pressurizing said fluid, a shallow body of water means for positioning and suspending the pressure vessel, an explosive tapered charge positioned a predetermined standoff distance from the pressure vessel within the body of water means, instrument means appropriately located on and within the test vessel and the pressure vessel for recording the underwater shockwave and the hydrostatic pressure upon exploding of the explosive tapered charge.

OBJECTS OF THE INVENTION

One object of this invention is to provide a deep depth pressure simulator means for determining the dual effects of nuclear type underwater shockwaves and hydrostatic pressures on a test vessel located in a shallow water means, but yielding deep depth data of underwater shockwaves and hydrostatic pressures.

Another object of the present invention is to provide a controlled testing environment, less costly, and shorter test time for deep depth simulation testing and determining the dual effects of deep depth underwater shockwaves and hydrostatic pressures on a test vessel located in a shallow water means; bubble pulse loading is avoided when tests are conducted in shallow water.

Other objects of the present invention will become apparent from the following description and drawings and from the operation itself as hereinafter described.

DETAIL DESCRIPTION OF THE DRAWINGS

Figure 1:
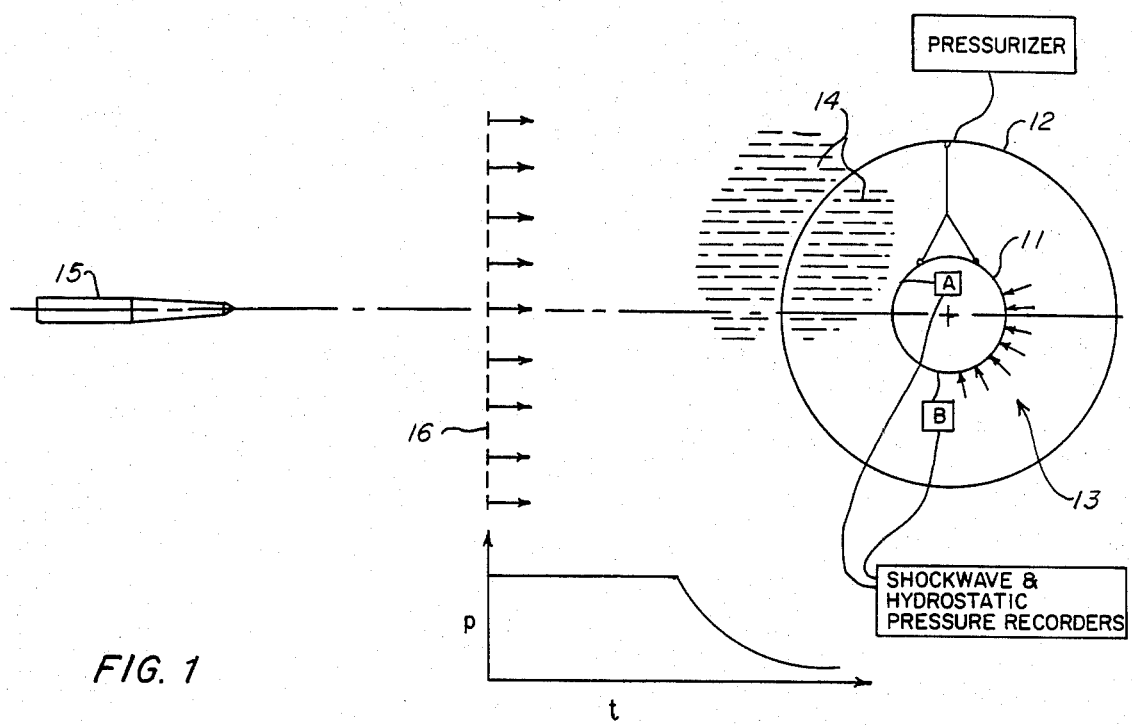
FIG. 1 is a perspective view of an embodiment of the invention.
Figure 2:
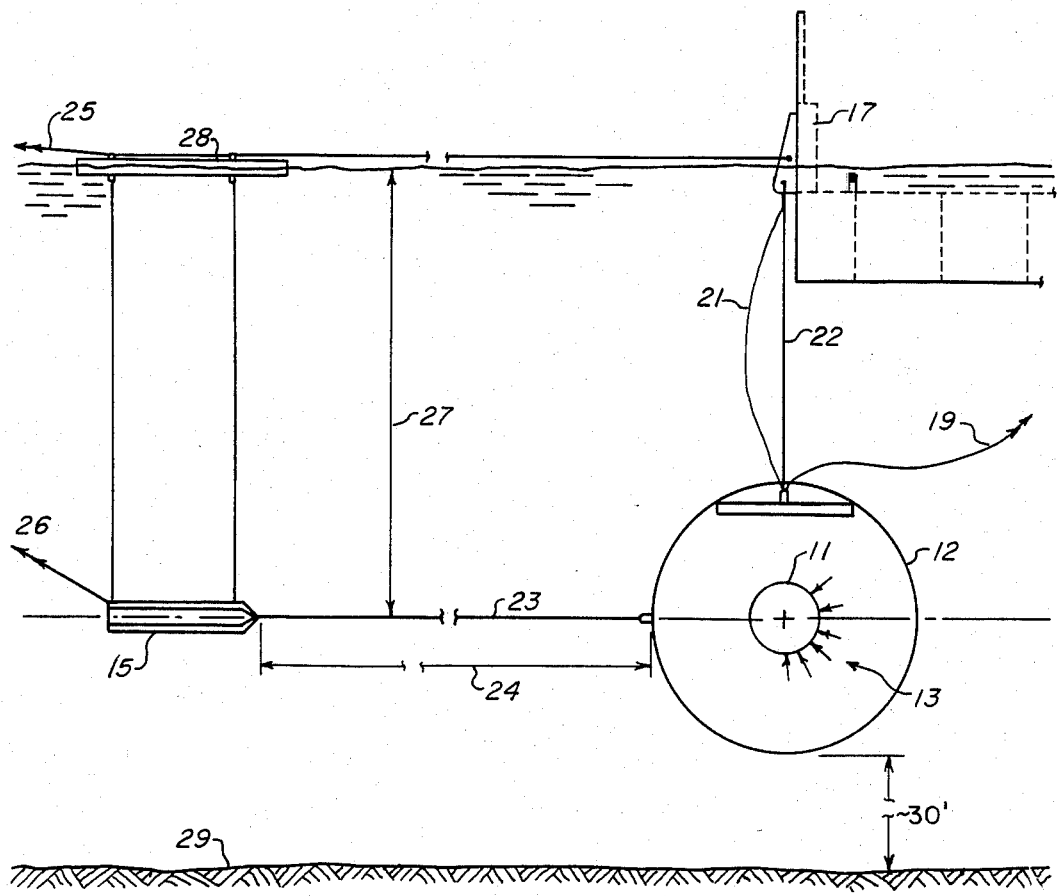
FIG. 2 is a perspective view illustrating the geometry in one test mode of an embodiment of the invention.

FIGS. 1 and 2 illustrate, in a perspective view, an embodiment of the invention, test pressure vessel 12 suspended from a floating shock platform 17 and having a model test vessel 11 suspended therein. Pressure 13 simulating by arrows a hydrostatic head on model test vessel 11. A tapered charge 15 is positioned at predetermined distance from test pressure vessel 12 in water 14 and creates shockwave front 16 upon detonation. In operation, the hydrostatic head pressure 13 is brought up to the required at-depth pressure desired and tapered charge 15 upon detonation simulates long duration shockwave front 16 pressure-time history of a nuclear type attack. The shockwave front 16 passes through test pressure vessel 12 wall, intervening water 14 outside test pressure vessel 12, and envelopes model test vessel 11 which is filled with air at atmospheric pressure. This provides simulation of shockwave front 16 and hydrostatic loading on model test vessel 11. Internal instrument A and external instrument B provide a record of the shockwave and hydrostatic pressure effects on and within test vessel 11. The depth of tapered charge 15 and test model vessel 11 can be selected to provide a desired shockwave front 16 duration time, avoid water surface effects and eliminate gas bubble pulse loadings. The size of test pressure vessel 12 is made sufficient in size to accommodate structural deformations and bodily motions of test model vessel 11.

FIG. 2 illustrates, in a perspective view, the geometry involved of the deep depth underwater simulator in one test mode of an embodiment of the invention. FIG. 2 illustrates, in detail, one test mode of an embodiment of the invention wherein the center of test model vessel 11 is positioned at a specific depth, and at a specific distance from tapered charge 15, and how it is positioned and maintained within test pressure vessel 12 and how test pressure vessel 12 is suspended and held in position by support pendants 22, catch pendants 21, and safety recovery pendants 19 and floating shock platform 17 which is used to suspend the test pressure vessel 12. To avoid clutter the pressurization means and the recording instrumentation are not shown explicitly in FIG. 2.

Figure 3:
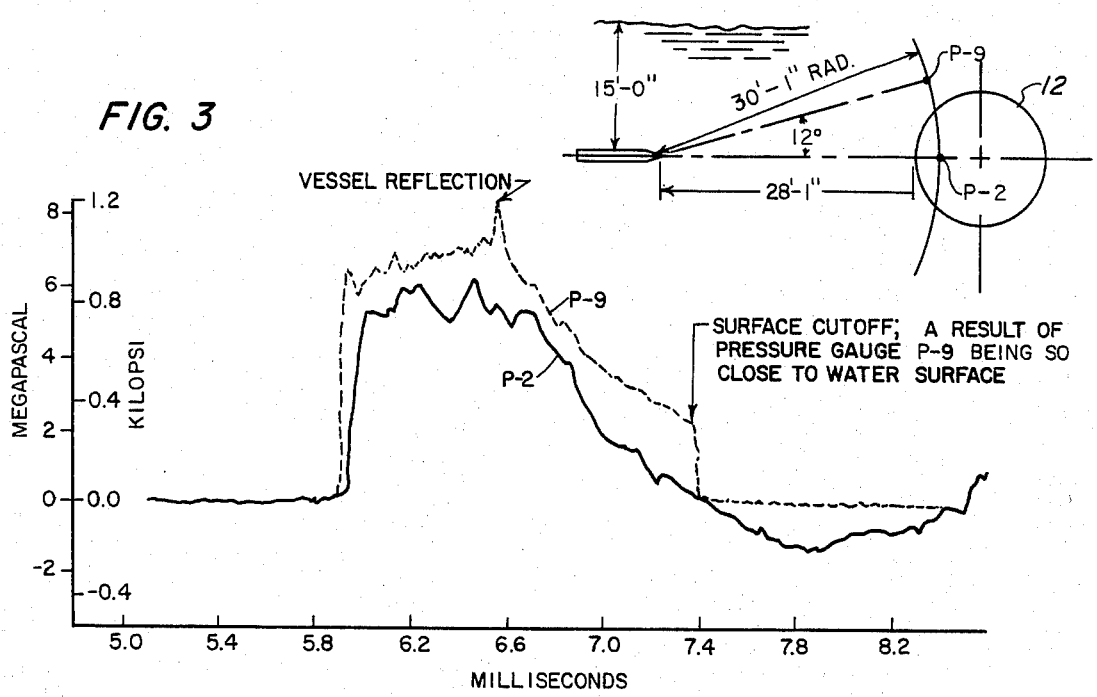
FIGS. 3 and 4 illustrate test result conducted in one test mode of an embodiment of the invention.
Figure 4:
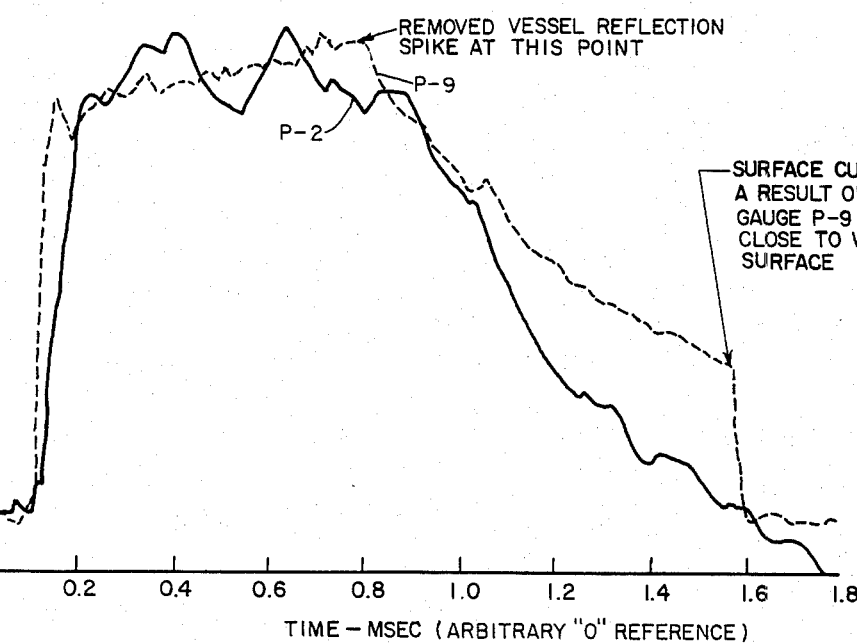

FIGS. 3 and 4 illustrate test results in one mode of an embodiment of the invention. FIG. 3 illustrates a comparison of pressure histories taken inside and outside pressurized test vessel 12. The pressure-time histories illustrate similar shape except the pressures are lower in the vessel at pressure point P-2 than at pressure point P-9. FIG. 3 also illustrates in the initial test that pressure fluctuation was noted within pressurized test vessel 12 at pressure point P-2 between about 6.1 and 6.6 milliseconds. It was further noted at approximately 7.4 milliseconds the pressure starts going negative, and then at approximately 8.5 milliseconds it starts to go positive. The cyclic effect continues for some time before it damps out completely. An air reservoir can be utilized that will provide a compressible medium which will eliminate, or at least significantly alleviate the pressure fluctuations.

FIG. 4 illustrates similar pressure-time histories showing shape comparisons only. The magnitude of the peak pressure can be controlled by varying either the tapered charge 15 weight and/or tapered charge 15 standoff distance from the test pressure vessel 12.

Obviously, many modifications and variations of the present invention are possible in light of the above teachings. It is therefore to be understood that within the scope of the appended claims, the invention may be practiced otherwise than as specifically described.

What is claimed is:

1. A deep depth underwater shockwave and hydrostatic pressure simulator means for determining the dual effects of nuclear type underwater shockwaves and hydrostatic pressures on a test vessel located in a shallow water means comprising:

a test vessel filled with air at atmospheric pressure and positioned and suspended within a pressure vessel, said pressure vessel containing fluid between the outer shell of the test vessel and the inner shell of the pressure vessel, a pressure means for pressurizing said fluid, a shallow body of water for positioning and suspending the pressure vessel therein, an explosive tapered charge with the smaller tapered portion facing the pressure vessel and positioned a predetermined standoff distance from the pressure vessel within the shallow body of water, instrument means located on and within the test vessel and the pressure vessel for recording the underwater shockwave and the hydrostatic pressure, upon exploding of the explosive tapered charge.

* * * * *